(12) United States Patent
Kim et al.

(10) Patent No.: US 6,254,884 B1
(45) Date of Patent: Jul. 3, 2001

(54) SOMATOTROPIN COMPOSITIONS MIXED WITH VITAMINS

(75) Inventors: Nam Joong Kim; Jephil Ryoo; Byoung Sun Chang, all of Taejon-si; Doo Kim, Chooncheon-si, all of (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/381,665

(22) PCT Filed: Jun. 11, 1998

(86) PCT No.: PCT/KR98/00153

§ 371 Date: Sep. 22, 1999

§ 102(e) Date: Sep. 22, 1999

(87) PCT Pub. No.: WO99/43342

PCT Pub. Date: Sep. 2, 1999

(30) Foreign Application Priority Data

Feb. 28, 1998 (KR) .................................................. 98-6601

(51) Int. Cl.⁷ .......................... A61K 38/16; A61K 9/127
(52) U.S. Cl. ........................... 424/450; 424/450; 424/489; 514/12; 514/633; 514/725; 426/72; 426/73; 426/74; 530/399
(58) Field of Search ..................................... 424/450, 489; 530/399; 426/73, 72, 74; 514/725, 633, 12

(56) References Cited

U.S. PATENT DOCUMENTS

| | | |
|---|---|---|
| 2,143,590 | 1/1939 | Scott et al. . |
| 2,174,862 | 10/1939 | Sahyun . |
| 2,491,537 | 12/1949 | Welch . |
| 2,507,193 | 5/1950 | Buckwalter . |
| 2,920,014 | 1/1960 | Peterson et al. . |
| 2,964,448 | 12/1960 | Anschel . |
| 3,016,330 | 1/1962 | Jacobsen . |
| 3,102,077 | 8/1963 | Christensen . |
| 3,676,557 | 7/1972 | Lachman et al. . |
| 3,852,422 | 12/1974 | Donini . |
| 3,869,549 | 3/1975 | Geller . |
| 4,075,333 * | 2/1978 | Josse ..................... 424/237 |
| 4,256,737 | 3/1981 | Nestor et al. . |
| 4,452,775 | 6/1984 | Kent . |
| 4,675,189 | 6/1987 | Kent et al. . |
| 4,761,289 | 8/1988 | Shalati et al. . |
| 4,765,980 | 8/1988 | DePrince et al. . |
| 4,786,501 | 11/1988 | Janski et al. . |
| 4,857,506 | 8/1989 | Tyle . |
| 4,861,580 | 8/1989 | Janoff et al. . |
| 4,863,736 | 9/1989 | Azain et al. . |
| 5,035,891 | 7/1991 | Runkel et al. . |
| 5,179,080 * | 1/1993 | Rothkopf ................. 514/12 |
| 5,198,422 | 3/1993 | Clark et al. . |
| 5,219,596 * | 6/1993 | Smith et al. ............... 426/2 |
| 5,228,697 | 7/1993 | Gulick et al. . |
| 5,356,635 | 10/1994 | Raman et al. . |
| 5,411,951 | 5/1995 | Mitchell . |
| 5,474,980 | 12/1995 | Mitchell . |
| 5,520,927 | 5/1996 | Kim et al. . |
| 5,595,752 | 1/1997 | Kasser et al. . |
| 5,767,080 * | 6/1998 | Beck et al. ............... 514/12 |
| 5,885,974 * | 3/1999 | Danielov ................. 514/109 |
| 5,916,588 * | 6/1999 | Popescu et al. ........... 424/450 |

FOREIGN PATENT DOCUMENTS

| | | |
|---|---|---|
| 193917 | 9/1986 | (EP) . |
| 0211691 | 2/1987 | (EP) . |
| 0213851 | 3/1987 | (EP) . |
| 0246540 | 11/1987 | (EP) . |
| 0314421 | 5/1989 | (EP) . |
| 0462959 | 12/1991 | (EP) . |
| WO8706828 | 11/1987 | (WO) . |
| WO9011070 | 10/1990 | (WO) . |
| WO9207556 | 5/1992 | (WO) . |
| WO9216194 | 10/1992 | (WO) . |
| WO9310758 | 6/1993 | (WO) . |

\* cited by examiner

*Primary Examiner*—Diana Dudash
*Assistant Examiner*—Shannam Sharareh
(74) *Attorney, Agent, or Firm*—Bachman & LaPointe, P.C.

(57) ABSTRACT

The present invention relates to a pharmaceutical compositions which comprises bioactive somatotropin and at least two kinds of lipid-soluble vitamins, and more particularly to a parenterally administered pharmaceutical composition which can solve inconvenience of administering somatotropin and lipid-soluble vitamins respectively and which shows the sustained effect of somatotropin and the synergic effect of somatotropin and lipid-soluble vitamins.

5 Claims, No Drawings

SOMATOTROPIN COMPOSITIONS MIXED WITH VITAMINS

FIELD OF THE INVENTION

The present invention relates to pharmaceutical composition which comprises bioactive somatotropin and at least two kinds of lipid-soluble vitamins, and more particularly to a parenterally administered pharmaceutical composition which can solve inconvenience of administering somatotropin and lipid-soluble vitamins respectively and which shows the sustained effect of somatotropin and the synergic effect of somatotropin and lipid-soluble vitamins.

BACKGROUND OF THE INVENTION

Recently, somatotropin has been produced massively by using genetic engineering techniques. Bovine somatotropin has been commercialized to increase the productivity of milk and porcine somatotropin has been commercialized to improve feed conversion ratio and to improve meat quality and so on.

Most of bioactive somatotropin formulations developed until now are the sustained-releasing type that a large amount of somatotropin is administered and released slowly only to avoid the inconvenience of daily administration. For examples, U.S. Pat. No. 5,411,951 and U.S. Pat. No. 5,474,980 disclose the sustained-releasing composition produced by adding a gelling agent such as aluminum monostearate into vegetable oil, and by gelatinizing oil by heating, and by mixing somatotropin homogeneously. These techniques have been already used to prepare sustained-releasing composition of antibiotics (U.S. Pat. No. 2,491,537, U.S. Pat. No. 2,507,193, U.S. Pat. No. 3,016,330), pamoate salts of oxazepin (U.S. Pat. No. 3,676,557) or relaxin (U.S. Pat. No. 2,964,448), parathyroid stimulating hormone (U.S. Pat. No. 3,869,549), luteinizing hormone releasing factor (U.S. Pat. No. 4,256,737), gonadotropin (U.S. Pat. No. 3,852,422) and insulin (U.S. Pat. No. 2,143,590, U.S. Pat. No. 2,174,862, U.S. Pat. No. 2,920,014, U.S. Pat. No. 3,102,077) and the like.

There are similar techniques for preparing sustained-releasing type by using oil. For example, EP 211691 discloses that somatotropin is mixed with wax and oil complex and EP 213851 suggests that sustained-releasing formulation is prepared by mixing somatotropin with oil and glyceride release-modifying agent available commercially. And EP 314421 discloses that sustained-releasing somatotropin composition is prepared by adding absorption-controlling material such as calcium stearate and dextran to oil. But this is a formulation that active ingredient has been substituted with somatotropin in the known oil-injection formulation.

In addition, the sustained-releasing techniques without using oil have been attempted. For example in EP 193917 somatotropin was mixed with water-soluble polysaccharides such as starch and dextrin to improve the sustained-releasing effect. But this formulation has shorter releasing time than other formulations mixed with oil and the somatotropin is unstable with water-soluble ingredients.

Another technique which does not use oil to prolong the releasing time has been described in U.S. Pat. No. 5,520,927. It discloses the formulation of tocopherol acetate and a release-delaying agent. However, in this case tocopherol acetate is used only for delaying the release of drug.

Different techniques from the above-mentioned have been attempted for sustained-releasing somatotropin formulations. U.S. Pat. No. 4,861,580 discloses sustained-releasing somatotropin formulation is prepared as a liposome type by using lipid-soluble material such as phosphatidyl choline, phosphatidyl ethanolamine and alpha-tocopherol hemisuccinate tris salt. And in U.S. Pat. No. 4,675,189 sustained-releasing somatotropin formulation was prepared as a microcapsule type by using bio-compatible polymer. And in U.S. Pat. No. 4,857,506 sustained-releasing somatotropin formulation is prepared as a multiple water-in oil-in water emulsion. But these are inadequate to be commercialized since the processes are so complex and high technologies are required. Furthermore the recovery rate to produce the desirable somatotropin is too low to be commercialized. In addition the somatotropin formulations prepared by the process are not stable and can not show the desirable sustained-release effect.

By using quite different methods, solid formulations which are implantable were prepared for improving the sustained-release of drugs. These techniques have been described in U.S. Pat. No. 4,452,775, U.S. Pat. No. 4,761,289, U.S. Pat. No. 4,765,980, U.S. Pat. No. 4,786,501, U.S. Pat. No. 4,863,736, U.S. Pat. No. 5,035,891, U.S. Pat. No. 5,198,422, U.S. Pat. No. 5,228,697, U.S. Pat. No. 5,356,635, U.S. Pat. No. 5,595,752 and EP 246540, 462959, PCT/US92/01877, PCT/US91/08129, PCT/US90/01340, PCT/AU87/00139 and the like. In these techniques solid somatotropin compositions were prepared and implanted into the animal body by surgical operation or by using special instruments which are expensive. The implanting techniques make it possible to release the desirable amount of bioactive somatotropin during the desirable period. However, the implanting process is too difficult to be performed and animals also feel uncomfortable due to the foreign substance.

The inventors of the present invention have conducted the intensive research for the sustained-release formulation of somatotropin to solve the above-mentioned problems. The inventors have found that somatotropin mixed with lipid-soluble vitamins at proper proportions shows the excellent sustained-release effect and additionally the synergic effect of the active ingredients by administering parenterally.

SUMMARY OF THE INVENTION

The object of the present invention is to provide the pharmaceutical compositions, when it is parenterally administered, which comprises somatotropin and at least two kinds of lipid-soluble vitamins, which has such a sustained-release effect that it reduces the pain and the labor cost due to the frequent injections and such a synergic effect of the active ingredients that it increases the productivity of milk in dairy cattle and reproduction efficiency and it decreases the somatic cell count in the milk, the incidence of mastitis and metabolic diseases of cattle.

DETAILED DESCRIPTION OF THE INVENTION

The present invention provides pharmaceutical compositions which comprises somatotropin and at least two kinds of lipid-soluble vitamins.

The lipid soluble vitamins which are used in the present invention contain vitamin A, vitamin D and vitamin E which are preferably used in preparing protein drugs since they make protein drugs such as somatotropin stable by preventing protein drugs from binding with water.

In addition to the above-stated advantage of the formulations, the vitamins have its own bioactivities described below.

Particularly, vitamin A promotes the sense of vision especially the adaptability to darkness which is related with rhodopsin and iodopsin of rod cell and cone cell sensing light on the retina. It can also improve abnormal dryness, denaturalization, keratinization and damage of mucosal membrane, ophthalmoxerosis and ophthalmomalacia and increase the resistance against various diseases. In addition, it has been reported to be an essential element in maintaining epidermal tissue and helping the growth of bone and teeth and it plays a great role as a growth stimulating hormone.

Vitamin D is an anti-rickets factor. When it is deficient, rickets, osteomalacia, osteopsathyrosis, tetany and the like can be caused. Since vitamin D is especially important for pregnant or lactating animals or and infant animals, it is necessary to administer by injection when it is deficient by provender.

Vitamin E is related to white muscle diseases. When it is deficient, white muscle diseases are caused, which partly changes the color of muscle fiber into gray and makes the muscles atrophied. The muscle atrophy provokes symptoms such as losing flexibility, stiffening and paralyzing of muscle. As the disease progresses, it becomes difficult to breathe. Resultantly animals having severe symptoms of the muscle atrophy became unable of lactation. Vitamin E is a anti-sterility vitamin for overcoming the sterility and it also promotes growth rate. And it helps reproducing processes, inhibits the abnormal development of muscle and prevents cerebromalacia, irregular activity of muscle, stiffness of muscle, malfunction and tonic spasm.

Hitherto, pharmaceutical compositions have been developed considering only the productivity for target animals and the convenience of dairy farmers. That is, when somatotropin is administered to animals, it is focused to reduce the dairy farmer's labor and costs of frequent dosage by elongating the releasing time. However, these pharmaceutical composition has been developed by focusing on the view only for the dairy farmers, which may cause unfavorable side effects since the health conditions of animals are neglected. It is known that the incidence of mastitis and a major disease of cow depends on the hygienic condition of surrounding environment, especially milking condition. But recently it has been reported that the incidence of mastitis depends on the total milk production of each dairy cow, that is, the more the productivity of milk increases, the more the incidence of mastitis increases. Therefore when somatotropin is used to increase the milk productivity, the proper management should be followed. To prevent mastitis hygienic condition should be necessary and the proper management program for the superior cow should be taken There are many factors to cause the mastitis as mentioned in the above, but it is more important to increase cow's resistance against bacteria. To increase the resistance against bacteria, proper drugs such as vitamins must be provided, in addition to the above-stated management. Practically, when vitamins are deficient the mucosal epithelial cells of papillary duct and papillary sinus are keratinized, which induces the infection and multiplication of bacteria. And the multiplied bacteria invade papillary sinus, which results in the severe inflammation. In addition the multiplied bacteria inhibit the synthesis of keratin, protecting material within papillary duct, and immunoglobulin. This causes the serious mastitis.

There are several methods for examining the mastitis, but the general method is to count the number of somatic cells in milk. The criteria for diagnosis is the number of somatic cells per 1 ml of milk. The lower the number the better the milk. And it can be passed that it is produced from cow without the clinical mastitis.

Therefore, in the present invention pharmaceutical compositions which comprises somatotropin and at least two kinds of lipid-soluble vitamins which do not affect the stability of somatotropin has been developed to enhance the productivity of milk and the health of animal by minimizing the side effects due to the increase of milk productivity.

Among lipid-soluble vitamins, vitamin A and vitamin D may show side effects when excessive amounts are administered. Thus the process for preparing the formulations should be made with extra care. Most of somatotropin formulations used recently have been manufactured as sustained releasing types which are administered every 2 weeks. The present invention also provides the formulation of sustained-releasing type having 2 weeks period. And the amount of vitamin A and vitamin D in the formulation has been controlled properly for preventing side effects of excessive administration and maximizing the synergic effect of the somatotropin and vitamins.

The somatotropin of various animals can be used in the present invention, but that of cow, pig or the like is preferred. And the natural somatotropin purified highly from pituitary gland of animals and somatotropin produced artificially by recombinant DNA technology also can be used.

In the pharmaceutical composition of the present invention, the somatotropin is contained in the range of 10–40 weight%, vitamin A is contained in the range of 500,000–5,000,000 units per 1 g of somatotropin. And vitamin D is contained in the range of 100,000–700,000 units per 1 g of somatotropin and vitamin E is contained in the range of 500–4,000 units per 1 g of somatotropin.

The pharmaceutical composition of somatotropin and lipid-soluble vitamins is prepared by adding lipid-soluble vitamins to a powdered somatotropin and homogenizing them. The powder-type somatotropin is prepared by lyophilizing only the somatotropin bulk solution, or by lyophilizing microparticles prepared by mixing delaying agent such as lecithin and the somatotropin bulk solution, or by lyophilizing the mixture of stabilizing agent such as sucrose, mannitol, trehalose and the somatotropin solution.

When the lyophilized somatotropin powder is used, water content and particle size should be considered. The water content concerned with the stability of the somatotropin should be below 3%. And the particle size concerned with the injection and the layer-separation after long storage should be below 10 $\mu$m in diameter. Therefore the lyophilized somatotropin should be ground to reduce the size when the size of the particle is above the range. At that time, the process can be performed with ball mill, air mill or the like, not changing the quality of the particle.

The pharmaceutical composition in the present invention is prepared by adding lipid-soluble vitamins to the powdered somatotropin prepared as the above-mentioned method in the proper ratio.

Preferred embodiments of the invention are illustrated as shown in the following examples.

However, it will be appreciated that those skilled in the art, on consideration of this disclosure, may make modifications and improvements within the spirit and scope of the present invention

EXAMPLES

Example 1

500 ml of bovine somatotropin (LG Chemical Ltd. Biotech. Institute) solution (60.5 mg/ml) was mixed with 10.08 g of lecithin by using a homogenizer for 30 min. and was grounded in a microfluidizer to make particles of less than 200 nm size of diameter. The suspension was filtrated by using a filter of 0.22 um pore size for sterilization and autoclaved, then dried in a freeze dryer. At that time the lyophilizing process was performed by using bottles in vacuum below 100 milli torr, at −70° C. and for about 48 hours. Bovine somatotropin-lecithin lyophilized as a powder form has 1.4% of water content which is measured in a boiling counter.

And 267 g of vitamin A palmitate (1 g =1,000,000 unit, viscous solution, BASF) and 1 g of vitamin $D_3$ (1 mg=40,000 unit, powder, Sigma) were quantified and mixed by using a magnetic bar.

Then 6.67 g of bovine somatotropin-lecithin (5 g bovine somatotropin, 1.67 g lecithin) as lyophilized powder was evenly mixed with 6.93 g of vitamin E acetate (1 mg=1 unit, viscous solution, ROCHE) and 7.53 g of the above mixture of vitamin A and vitamin $D_3$ in a homogenizer. Then the mixed composition was put in a vacuum chamber for 6 hours to remove air bubbles.

Example 2

The pharmaceutical composition was prepared by performing the same process of Example 1 with different component ratios. 6.67 g of bovine somatotropdn-lecithin as lyophilized powder was evenly mixed with 9.44 g of vitamin E acetate and 5.02 g of the mixture of vitamin A and vitamin $D_3$ in a homogenizer.

Example 3

The pharmaceutical composition was prepared by performing the same process of Example 1. 6.67 g of bovine somatotropin-lecithin as lyophilized powder was evenly mixed with 3.16 g of vitamin E acetate and 11.30 g of the mixture of vitamin A and vitamin D.

Example 4

The pharmaceutical composition was prepared by performing the same process of Example 1. 6.67 g of bovine somatotropin-lecithin as lyophilized powder was evenly mixed with 11.95 g of vitamin E acetate and 2.51 g of the mixture of vitamin A and vitamin $D_3$.

Example 5

The pharmaceutical composition was prepared by performing the same procedure of Example 1. 3.34 g of bovine somatotropin-lecithin as lyophilized powder was evenly mixed with 6.93 g of vitamin E acetate and 7.53 g of the mixture of vitamin A and vitamin $D_3$.

Comparative Example 1

The composition was prepared by performing the same process of Example 1. 6.67 g of bovine somatotropin-lecithin as lyophilized powder was mixed with 14.46 g of vitamin E acetate.

Comparative Example 2

The composition was prepared by performing the same process of Example 1. Precisely 3.34 g of cow somatotropin-lecithin as lyophilized powder was mixed with 14.46 g of vitamin E acetate.

Example 6

The animal test was performed by using the somatotropin compositions which were prepared in Example 1, 2, 3, 4 and Comparative Example 1 and by utilizing the porcine somatotropin powder without lecithin instead of the above bovine somatotropin-lecithin powder. As experimental animals, rats having genetic dwarfism were utilized.

Female, 8-week old dwarf rats weighed about 100 g were used. The interval between light and dark was 12 hours and water and feed were provided freely. 4 rats in a cage were used for examining the effects of one composition. The rats were separated randomly according to the average weight during 3 days and the standard error measured before administration. The average weight during the 3 days was considered as a standard weight. 0.04 ml of each composition (corresponding to 10 mg of porcine somatotropin) was subcutaneously injected in the abdominal part and then the weights were measured at the determined time every day for 7 consecutive days. As a comparative group, 4 dwarf rats without the injection were examined and the weights were measured during the above period by the same process. The cumulative mean weight gain was indicated in table 1 which was measured at the animal group respectively and cumulatively.

TABLE 1

| Day | Example 1 | Example 2 | Example 3 | Example 4 | Comp. Example | Control |
|---|---|---|---|---|---|---|
| 1 | 9.95 ± 1.77 | 10.18 ± 0.08 | 9.34 ± 0.29 | 10.66 ± 0.90 | 9.66 ± 0.69 | 0.88 ± 1.61 |
| 2 | 17.35 ± 1.85 | 17.93 ± 0.08 | 17.74 ± 0.86 | 17.71 ± 1.40 | 18.61 ± 0.87 | 0.68 ± 1.08 |
| 103 | 24.15 ± 1.01 | 25.16 ± 0.90 | 24.37 ± 0.77 | 23.76 ± 1.81 | 24.30 ± 0.98 | 2.62 ± 1.05 |
| 4 | 30.95 ± 0.54 | 32.38 ± 1.01 | 31.27 ± 0.68 | 29.81 ± 2.29 | 29.98 ± 1.09 | 3.55 ± 1.03 |
| 5 | 37.03 ± 1.44 | 38.33 ± 1.39 | 36.42 ± 0.17 | 33.98 ± 4.11 | 34.53 ± 0.98 | 3.70 ± 0.63 |
| 6 | 4.40 ± 2.04 | 44.01 ± 1.25 | 4.22 ± 0.60 | 38.48 ± 3.98 | 40.46 ± 1.57 | 6.45 ± 0.97 |
| 7 | 40.58 ± 1.73 | 41.23 ± 1.43 | 40.47 ± 1.93 | 35.13 ± 2.90 | 38.48 ± 1.42 | 5.08 ± 0.64 |

(mean + standard error: g)

As shown in the table 1, in the group administered the pharmaceutical composition of the present invention, the weights of animals increases more than about 30 g than that of the control group at day 7.

Example 7

Experiment has been conducted to the cow which are main target animals of the present pharmaceutical composition by using the pharmaceutical compositions prepared in Example 1, 2, 3 and Comparative Example 1. As experimental cow, Holstein species having the parity more than twice and the lactation day between 65–186 days were selected. Each cow was diagnosed to be healthy before the experiment and particularly mastitis was examined by culturing bacteria respectively. In order to make the milk yield of each group evenly at the starting point of the experiment, the mean dairy milk yield of each cow was calculated and then 45 cows are divided into 5 groups, in order for each group to have similar milk yield. At the starting point, the milk yield, lactation day and parity were depicted in table 2. In the each group, the mean yield of milk, the parity and the lactation day were in the narrow range of 27.4±2.9–27.8±3.1 kg, 2–7 parity and 65–186 days respectively.

TABLE 2

| index | | min. value | max. value | mean | standard error |
|---|---|---|---|---|---|
| control | milk yield (kg/day) | 15.3 | 38.2 | 27.8 | 3.1 |
| | parity | 2 | 6 | 3.4 | 0.5 |
| | lactation day | 85 | 185 | 137.7 | 11.4 |
| Example 1 | milk yield | 21.1 | 38.1 | 27.8 | 2.1 |
| | parity | 2 | 6 | 3.4 | 0.4 |
| | lactation day | 65 | 186 | 136.3 | 12.8 |
| Example 2 | milk yield | 16.1 | 40.3 | 27.7 | 2.9 |
| | parity | 2 | 6 | 3.8 | 0.5 |
| | lactation day | 88 | 186 | 138.4 | 12.1 |
| Example 3 | milk yield | 20.0 | 34.0 | 27.8 | 1.6 |
| | parity | 2 | 5 | 3.8 | 0.3 |
| | lactation day | 66 | 174 | 140.4 | 11.3 |
| Comp. Example 1 | | 16.9 | 37.3 | 27.4 | 2.9 |
| | | 2 | 7 | 3.9 | 0.6 |
| | | 79 | 177 | 127.7 | 13.1 |

Considering the above parity, lactation day and the like, 45 cow were separated into 5 groups containing 9 heads per group, particularly negative control group where nothing had been administered, group 1 administered with 500 mg (bovine somatotropin 250 mg/ml) of the pharmaceutical composition prepared in Example 1 and mixed with vitamin A, D and E (A: 750,000 unit; D: 112,500 unit; E: 693 unit), group 2 administered with 500 mg (bovine somatotropin 250 mg/ml) of the pharmaceutical composition prepared in Example 2 and mixed with vitamin A, D and E (A: 500,000 unit; D: 75,000 unit; E: 944 unit), group 3 administered with 500 mg (bovine somatotropin 250 mg/ml) of the pharmaceutical composition prepared in Example 3 and mixed with vitamin A, D and E (A: 1,125,000 unit; D: 168,750 unit; E: 316 unit) and the other comparative group 1 administered with 500 mg (bovine somatotropin 250 mg/ml) of the pharmaceutical composition prepared in Comparative Example 1. These compositions were injected subcutaneously through right or left ischiorectal fossa alternatively. Before the injection, the injection sites were sterilized completely by using 70% EtOH cotton containing iodine and after the injection, efficient massage was performed for about 30 seconds in order to spread the drug evenly. During the experimental period, the amount of concentrated diets provided was controlled according to that of milk produced and corn silage and alfalfy hay was provided freely. The other condition were controlled by the regulations of the general experimental farm. During 1 week before injection, milk yield produced daily were measured in order to get the standard value of milk yield and compared with the daily milk yield produced after the injection. And the contents of milk fat, milk protein, milk lactose and milk solid not fat) in the milk collected from each cow were analyzed by using the automatic milk analyzer (Milk-Scan 133B, Foss Electric, Denmark). The above milk was collected in the morning and afternoon respectively and was mixed according to the ratio of the productivity at the 1 week before injection and every 4 week after the injection. During the total period, each cow's milk was also collected sterilely every 4 week, inoculated into sheep blood agar media and cultured for identifying the species of bacteria in order to diagnose mastitis, And the results were analyzed. And strip cup test and sterilization of udder were also performed before and after every milking. As an index of mastitis, somatic cell count was measured in the each milk collected before and after the injection by using Foss-O-matic Somatic Cell Count (Foss Electric, Denmark). The milking procedure was adopted from regulations of the general experimental farm and the operating conditions of the milking machines was checked every month before the experiment. During the overall period body condition score was measured every 4 week. The results were shown in table 3. The table 3 indicated milk yield, increase ratio of milk yield to that of comparative group, component variation of milk, body condition score and index of mastitis (somatic cell count).

TABLE 3

| | control | Example 1 | Example 2 | Example 3 | Comp. Example 1 |
|---|---|---|---|---|---|
| milk yield (kg/day) | 21.4 | 26.0 | 27.2 | 27.6 | 26.2 |
| increase rate (%) of milk yield to comparative group | — | 21.5 | 27.1 | 29.0 | 22.4 |
| milk fat (%) | 3.44 | 3.45 | 3.59 | 3.46 | 3.28 |
| milk protein (%) | 3.41 | 3.46 | 3.45 | 3.44 | 3.37 |
| milk lactose (%) | 4.88 | 4.85 | 4.78 | 4.93 | 4.69 |
| milk solid not fat (%) | 9.07 | 9.01 | 9.08 | 9.13 | 8.81 |
| somatic cell count ($10^3$/ml) | 557 | 348 | 507 | 291 | 463 |
| body condition score | 3.0 | 2.8 | 2.8 | 2.7 | 2.7 |

As shown above, the pharmaceutical compositions of the present invention comprising somatotropin and at least 2 kinds of lipid-soluble vitamins enhance the growth of animal and the milk yield of cow and improved the health outstandingly by preventing mastitis, a major problem.

Considering the general practice of administering somatotropin and vitamins by separate injections, the pharmaceutical composition of the present invention has many advantages of reducing costs, labor and pains of target animals due to single injection.

As described above, the present invention relates to the pharmaceutical compositions comprising somatotropin and at least two kinds of lipid-soluble vitamins, which can be administered parenterally such as by injection. The compositions has sustained and synergic effect by administering somatotropin and vitamins at once, thus increase the milk yield and the reproduction performance and reduce the incidence of metabolic diseases such as mastitis and reduce the frequency of administration. Therefore they also effectively reduce costs, labor and pains of target animals by low frequency of administration.

What is claimed is:

1. A method for increasing milk production and decreasing incidence of mastitis of dairy cattle, which comprises the steps of:
   (a) providing dairy cattle; and
   (b) administering to said dairy cattle a pharmaceutical composition comprising somatotropin, a delaying agent and at least two kinds of lipid-soluble vitamins which are selected from the group consisting of vitamin A in the range of 500,000–5,000,000 units per 1 g of somatotropin, vitamin D in the range of 100,000–700,000 units per 1 g of somatotropin, and vitamin E in the range of 500–4,000 units per 1 g of somatotropin.

2. The method according to claim 1 wherein the somatotropin is bovine somatotropin or porcine somatotropin.

3. The method according to claim 1 wherein the somatotropin is bovine somatotropin produced by recombinant DNA technology.

4. The method according to claim 1 wherein the somatotropin is contained in the range of 10–40 wt %.

5. The method according to claim 1, wherein the delaying agent is lecithin.

* * * * *